United States Patent [19]

Albrecht et al.

[11] 4,151,277
[45] Apr. 24, 1979

[54] NON-GLYCOSIDIC THEOPHYLLINE-SUGAR DERIVATIVES

[75] Inventors: Hans P. Albrecht, Weinheim; Ludwig Friedrich, Bruehl; Frank Zimmermann, Neustadt, all of Fed. Rep. of Germany

[73] Assignee: BASF Aktiengesellschaft, Ludwigshafen, Fed. Rep. of Germany

[21] Appl. No.: 885,646

[22] Filed: Mar. 13, 1978

[30] Foreign Application Priority Data

Apr. 2, 1977 [DE] Fed. Rep. of Germany ....... 2714883

[51] Int. Cl.² ................ A61K 31/70; C07G 3/00
[52] U.S. Cl. ............................ 424/180; 536/4; 536/53; 536/24
[58] Field of Search ............... 536/53, 18, 24, 4

[56] References Cited

U.S. PATENT DOCUMENTS 2,993,039  7/1961  Schroeder ................. 536/24
3,380,996  4/1968  Honjo et al. ............... 536/24

Primary Examiner—Johnnie R. Brown
Assistant Examiner—Blondel Hazel
Attorney, Agent, or Firm—Curtis, Morris & Safford

[57] ABSTRACT

Hypolipemic non-glycosidic theophylline-sugar compounds having the formula

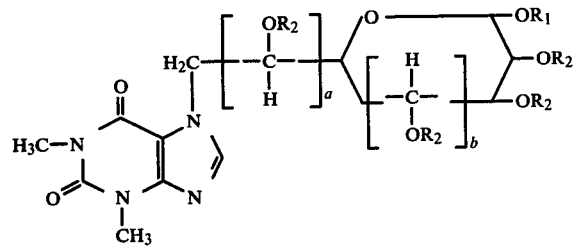

are disclosed, as are a method for making them and methods and compositions for treating hyperlipemia with the compounds.

16 Claims, No Drawings

NON-GLYCOSIDIC THEOPHYLLINE-SUGAR DERIVATIVES

The present invention relates to non-glycosidic theophylline-sugar derivatives, to a method for making them, and to pharmaceutical compositions containing these derivatives.

For the treatment of elevated blood fat levels, clofibrate [2-(p-chlorophenoxy)-2-methylpropionic acid ethyl ester] is predominantly employed in therapy. However, this substance leads to an increase in the size of the liver (hepatomegaly), cf. R. Howe, Hypolipidemia Agents in "Advances in Drug Research", Vol. 9, page 7, Academic Press (1974). Now, compounds have been found which are superior to clofibrate in their lipid-reducing and cholesterol-reducing properties and which do not lead to a change in the liver.

More in particular, the present invention relates to non-glycosidic theophylline-sugar derivatives of the formula

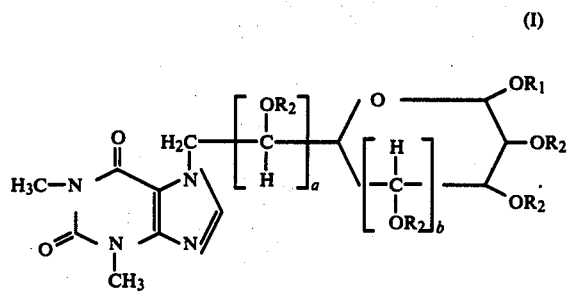

(I)

wherein $R_1$ taken alone is alkyl having 1-4 carbon atoms, $R_2$ taken alone is hydrogen, aliphatic acyl having 1-4 carbon atoms, benzoyl, nicotinoyl or clofibrinyl, and wherein any two adjacent $R_2$ groups taken together or $R_1$ and adjacent $R_2$ taken together may also represent an acetal or ketal protective group, and wherein a and b are 0 or 1, but a and b may not both be 1.

The invention also relates to a method for making compounds of the above-identified formula, which method comprises reacting theophylline with a sugar derivative of the formula

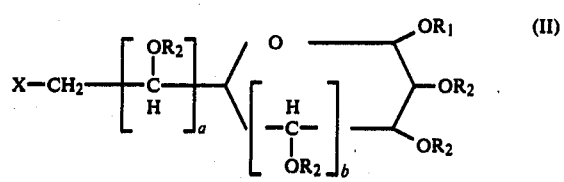

(II)

wherein X is a reactive leaving group, preferably methanesulfonyl or toluenesulfonyl, $R_1$, $R_2$, a and b have their aforementioned meanings and wherein, optionally, acyl groups or acetal or ketal protective groups are subsequently removed by cleavage.

As acetal and ketal protective groups, those materials suitable for protecting neighboring hydroxy groups in the cis-position are employed, preferably those having up to 5 carbon atoms. Isopropylidene is particularly suitable.

Finally, the invention relates to pharmaceutical compositions which contain compounds of formula (I) as the active ingredient.

The preparation of the new compounds from theophylline and the sugar derivatives of formula (II) takes place in the presence of a base in a dipolar aprotic solvent at about 50°-150° C. As bases, which are preferably used in an amount equivalent to the amount of sugar derivative, sodium bicarbonate, sodium carbonate, sodium hydroxide, sodium hydride, potassium bicarbonate, potassium carbonate, potassium hydroxide, and barium hydroxide are especially to be considered. Dimethylformamide, dimethylsulfoxide, acetonitrile, ethylene glycol dimethyl ether, and tetrahydrofurane are particularly suitable as solvents.

The sugar derivatives used as starting materials are prepared by selective mesylation or tosylation of the reactive primary hydroxy groups according to Cramer, "Methods in Carbohydrate Chemistry", Vol. II, page 244, Academic Press, (1963) and subsequent reaction with a corresponding acid chloride or acid anhydride in the conventional fashion.

The new compounds have good lipid-lowering properties. They are, thus, valuable therapeutic agents for the treatment of disturbances of the fat metabolism.

The lipid-lowering efficacy was demonstrated in analogy to known methods [cf. the article by Wahlefeld in Bergmeyer, "Methoden der enzymatischen Analyse", Vol. 11, Verlag Chemie, Weinheim (1974); Allain et al., Clin. Chem., 20, 470 (1974); and Roeschlau et al., Z. Klin. Chem. Klin. Biochem. 12, 226 (1974)] using normolipemic and hyperlipemic rats in short term and long term studies. Clofibrate served as the comparison compound.

Table

| Number | Example | Substance | Time of Treatment (Days) | Reduction In Serum Triglycerides (%) |
|---|---|---|---|---|
| 1 | 4 | Methyl-5-desoxy-5-(theophyll-7-yl)-β-D-ribofuranoside | 7 | 40.9 |
| 2 | 2 f | Methyl-5-desoxy-5-(theophyll-7-yl)-2,3-di-O-nicotinoyl-β-D-ribofuranoside | 7 | 46.5 |
| 3 | 2 e | 6-Desoxy-6-(theophyll-7-yl)-3,5-di-O-clofibrinyl-1,2-O-isopropyliden-α-D-glucofuranoside | 3 | 26.1 |
| 4 | 2 c | 6-Desoxy-6-(theophyll-7-yl)-1,2-O-isopropyliden-3,5-di-O-nicotinoyl-α-D-glucofuranoside | 3 | 71.4 |
| 5 | 1 | Methyl-6-desoxy-6-(theophyll-7-yl)-2,3,4-tri-O-nicotinoyl-α-D-glucopyranoside | 3 | 79.2 |
| 6 | | Clofibrate | 3 | 0.2 |

Table -continued

| Number | Example | Substance | Time of Treatment (Days) | Reduction In Serum Triglycerides (%) |
|---|---|---|---|---|
| 7 | | Clofibrate | 7 | 4.6 |

As the Table shows, the compounds clearly reduce serum triglycerides in normolipemic rats at a dosage of 160 mg/kg per os, both after 3 days' treatment and after 7 days' treatment.

The most effective substances are shown by these tests to be the compounds of following Examples 1 and 2c.

In addition, the new substances hinder an increase in serum triglycerides induced by fructose, whereas clofibrate shows this effect only at the beginning of treatment. Further, treatment with the new substances—in contrast to clofibrate—leads neither to an increase in the alkaline phosphatases in the blood nor to an increase in the weight of the liver.

The new compounds are well tolerated. No neurotoxic symptoms could be observed up to a dosage of 160 mg/kg per os per day. At this dosage, clofibrate produces clear symptoms.

The new compounds thus possess good serum triglyceride-lowering properties, show no hepatotoxic side effects, and are well tolerated. They can thus be used as therapeutic agents for hyperlipemia.

The new substances should be used in a dosage of 0.2—2 grams per patient per day. As administration forms, syrup, capsules, tablets, dragées and the like are suitable. The usual pharmaceutically acceptable solid and liquid carriers may be employed.

A better understanding of the present invention and of its many advantages will be had by referring to the following specific Examples, given by way of illustration.

EXAMPLE 1

17.4 g (50 m mol) of methyl-6-O-toluenesulfonyl-α-D-glucopyranoside in 200 ml of pyridine are combined with stirring at 0° C. with 35.5 g (250 m mol) of nicotinic acid chloride. The reaction mixture is subsequently stirred for 18 hours at room temperature with exclusion of atmospheric moisture. While cooling with ice, 100 ml of methanol are added. After 30 minutes, the reaction mixture is distributed between water and chloroform at room temperature. The organic phase is washed with saturated sodium bicarbonate solution and with water, dried over sodium sulfate, and evaporated. The residue remaining after co-evaporation with toluene is crystallized from methylene chloride/diethyl ether. 25.9 g of methyl-2,3,4-tri-O-nicotinoyl-6-O-toluenesulfonyl-α-D-glucopyranoside are obtained.

6.3 g (35 m mol) of anhydrous theophylline in 200 ml of dimethylformamide are combined under a nitrogen atmosphere while stirring with 0.9 g (37.5 m mol) of sodium hydride. Subsequently, 23.2 g (35 m mol) of 2,3,4-tri-O-nicotinoyl-6-O-toluenesulfonyl-methyl-α-D-glucopyranoside are added. The reaction mixture is stirred under nitrogen for 16 hours at 90° C—100°. The mixture is subsequently evaporated in vacuum. The residue is distributed between chloroform and water and the organic phase is washed with water, dried over sodium sulfate, and evaporated. The residue is purified by chromatography on a silica gel column (elution with methylene chloride/methanol, 15:1) or by recrystallization. 14.75 g (63%) of methyl-6-desoxy-6-(theophyll-7-yl)-2,3,4-tri-O-nicotinoyl-α-D-glucopyranoside are obtained, m.p.=130° C.–133° C. (methylene chloride/diethyl ether).

$C_{32}H_{29}N_7O_{10}$ (MW=671.6) Calc. C 57.22 H 4.35 N 14.59 Found C 57.1 H 4.5 N 14.6

EXAMPLE 2

Proceeding as in Example 1, 42 g (90%) of methyl-2,3,4-tri-O-clofibrinyl-6-O-toluenesulfonyl-α-D-glucopyranoside are obtained in amorphous form from methyl-6-O-toluenesulfonyl-α-D-glycopyranoside (17.4 g, 50 m mol) and clofibrinic acid chloride (58.3 g. 250 m mol) after conventional working up and chromatography on a silica gel column (elution with methylene chloride/methanol, 15:1).

Proceeding according to Example 1, and after column chromatography on silica gel (elution with methylene chloride/methanol, 15:1), 16 g (38%) of methyl-6-desoxy-6-(theophyll-7-yl)-2,3,4-tri-O-clofibrinyl-α-D-glucopyranoside are obtained from 8.1 g (45 m mol) of theophylline and 42 g (45 m mol) of methyl-2,3,4-tri-O-clofibrinyl-6-O-toluenesulfonyl-α-D-glucopyranoside. m.p.=137° C.–140° C. (diethyl ether).

$C_{44}H_{47}Cl_3N_4O_{13}$ (MW=946) Calc. C 55.85 H 5.01 Cl 11.24 N 5.92 Found C 55.7 H 5.0 Cl 11.5 N 5.8

Proceeding as in Examples 1 and 2, the following were prepared with about the same yield.

(a) Methyl-6-desoxy-6-(theophyll-7-yl)-2,3,4-tri-O-acetyl-α-D-glucopyranoside, m.p.=173° C.–176° C. (methylene chloride/diethyl ether/hexane)

$C_{20}H_{26}N_4O_{10}$ (MW=482.4) Calc. C 49.79 H 5.43 N 11.61 Found C 49.7 H 5.4 N 11.6

(b) Methyl-6-desoxy-6-(theophyll-7-yl)-α-D-glucopyranoside, m.p.=198° C.–200° C. (methylene chloride - with a trace of methanol/diethyl ether/hexane)

$C_{14}H_{20}N_4O_7$ (MW=356.3) Calc. C 47.19 H 5.66 N 15.72 Found C 47.5 H 5.9 N 15.7

(c) 6-Desoxy-6-(theophyll-7-yl)-1,2-O-isopropyliden-3,5-di-O-nicotinoyl-α-D-glucofuranoside, amorphous $C_{28}H_{28}N_6O_9$ (MW=592.4) Calc. C 56.77 H 4.76 N 14.19 Found C 56.7 H 4.9 N 14.0

6-Desoxy-6-(theophyll-7-yl)-1,2-O-isopropylidene-α-D-glucofuranoside, m.p.=94° C.–100° C. (methylene chloride/diethyl ether/hexane)

$C_{16}H_{22}O_7N_4$ (MW=382.4) Calc. C 50.25 H 5.80 N 14.66 Found C 50.4 H 6.0 N 14.7

(e) 6-Desoxy-6-(theophyll-7-yl)-3,5-di-O-clofibrinyl-1,2-O-isopropyliden-α-D-glucofuranoside, amorphous $C_{36}H_{40}Cl_2N_4O_{11}$ (MW=775.6) Calc. C 55.74 H 5.20 N 7.22 Cl 9.14 Found C 55.8 H 5.3 N 7.2 Cl 9.2

(f) Methyl-5-desoxy-5-(theophyll-7-yl)-2,3-di-O-nicotinyl-β-D-ribofuranoside, m.p.=187° C.–189° C. (methylene chloride/diethyl ether)

$C_{25}H_{24}N_6O_8$ (MW=536.5) Calc. C 55.97 H 4.51 N 15.67 Found C 55.9 H 4.8 N 15.3

(g) Methyl-5-desoxy-5-(theophyll-7-yl)-2,3-di-O-clofibrinyl-β-D-ribofuranoside, m.p.=153° C.–155° C. (methylene chloride/diethyl ether/hexane)

$C_{33}H_{36}N_4O_{10}Cl_2$ (MW=719.6) Calc. C 55.08 H 5.04 N 7.79 Cl 9.85 Found C 55.2 H 5.1 N 7.6 Cl 10.0

(h) Ethyl-6-desoxy-6-(theophyll-7-yl)-2,3,4-tri-O-nicotinoyl-α-D-glucopyranoside, amorphous $C_{33}H_{31}N_7O_{10}$ (MW=685.6) Calc. C 57.80 H 4.56 N 14.30 Found C 57.6 H 4.8 N 14.3

(i) Methyl-6-desoxy-6-(theophyll-7-yl)-2,3,4-tri-O-benzoyl-α-D-glucopyranoside, m.p.=124° C.–127° C.

$C_{35}H_{32}N_4O_{10}$ (MW=668.6) Calc. C 62.87 H 4.82 N 8.38 Found C 62.9 H 4.9 N 8.3

EXAMPLE 3

De-acetylation of 4.8 g (10 m mol) of methyl-6-desoxy-6-(theophyll-7-yl)-2,3,4-tri-O-acetyl-α-D-glucopyranoside (Example 2a) with methanolic NH$_3$ (2 hours, room temperature), evaporation of the reaction solution, chromatography of the residue on silica gel (elution with methylene chloride/methanol, 7:1), and crystallization from methylene chloride/methanol/ether/hexane give 2.9 g (81%) of methyl-6-desoxy-6-(theophyll-7-yl)-α-D-glucopyranoside (compare Example 2b).

EXAMPLE 4

Proceeding as in Example 1, 90 g of methyl-5-desoxy-5-(theophyll-7-yl)-2,3-O-isopropylidene-β-D-ribofuranoside are obtained from 54 g (300 m mol) of theophylline and 107.3 g (300 m mol) of methyl-2,3-O-isopropylidene-6-O-toluenesulfonyl-β-D-ribofuranoside after column chromatography (elution with methylene chloride/methanol, 20:1). After cleavage of the isopropylidene protective group with 0.5 N HCl in 800 ml of methanol/water, 1:1 (48 hours, room temperature), neutralization with a basic ion exchanger, evaporation, and chromatographic purification of the residue on silica gel (elution with methylene chloride/methanol, 10:1), 43 g (44%) of methyl-5-desoxy-5-(theophyll-7-yl)-β-D-ribofuranoside are obtained. m.p.=182° C.–184° C. (methanol)

$C_{13}H_{18}N_4O_6$ (MW=326.0) Calc. C 47.85 H 5.56 N 17.17 Found C 48.0 H 5.6 N 17.2

EXAMPLE 5

A granulate of the following composition is prepared in the usual way:

300 g of methyl-6-desoxy-6-(theophyll-7-yl)-2,3,4-tri-O-nicotinoyl-α-D-glucopyranoside 221 g of corn starch 20 g of gelatin 60 g of lactose 35 g of talc 3.5 g of "Aerosil" (chemically pure silicic acid in submicroscopically fine division)

10.5 g of potato starch (as a 6% paste)

650 mg portions of the granulate were filled into hard gelatin capsules.

What is claimed is:

1. A theophylline-sugar compound of the formula

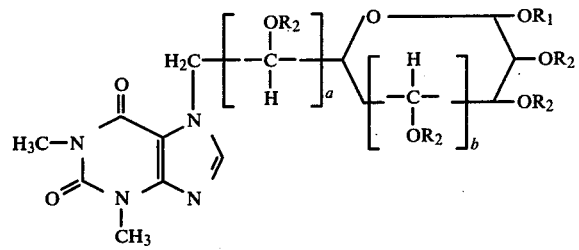

wherein R$_1$ taken alone is alkyl having 1 to 4 carbon atoms, R$_2$ taken alone is hydrogen, aliphatic acyl having 1–4 carbon atoms, benzoyl, nicotinoyl, or clofibrinyl; wherein any two adjacent R$_2$ groups taken together or R$_1$ and adjacent R$_2$ taken together may also be an acetal or ketal protective group having up to 5 carbon atoms; and wherein a and b are the integer 0 or 1 but a and b may not both be 1.

2. A compound as in claim 1 wherein said protective group is isopropylidene.

3. A compound as in claim 1 which is methyl-6-desoxy-6-(theophyll-7-yl)-2,3,4-tri-O-nicotinoyl-α-D-glucopyranoside.

4. A compound as in claim 1 which is methyl-6-desoxy-6-(theophyll-7-yl)-2,3,4-tri-O-clofibrinyl-α-D-glucopyranoside.

5. A compound as in claim 1 which is methyl-6-desoxy-6-(theophyll-7-yl)-2,3,4-tri-O-acetyl-α-D-glucopyranoside.

6. A compound as in claim 1 which is methyl-6-desoxy-6-(theophyll-7-yl)-α-D-glucopyranoside.

7. A compound as in claim 1 which is 6-desoxy-6-(theophyll-7-yl)-1,2-O-isopropyliden-3,5-di-O-nicotinoyl-α-D-glucofuranoside.

8. A compound as in claim 1 which is 6-desoxy-6-(theophyll-7-yl)-1,2-O-isopropyliden-α-D-glucofuranoside.

9. A compound as in claim 1 which is 6-desoxy-6-(theophyll-7-yl)-3,5-di-O-clofibrinyl-1,2-O-isopropyliden-α-D-glucofuranoside.

10. A compound as in claim 1 which is methyl-5-desoxy-5-(theophyll-7-yl)-β-D-ribofuranoside.

11. A compound as in claim 1 which is methyl-5-desoxy-5-(theophyll-7-yl)-2,3-di-O-nicotinoyl-β-D-ribofuranoside.

12. A compound as in claim 1 which is methyl-5-desoxy-5-(theophyll-7-yl)-2,3-di-O-clofibrinyl-β-D-ribofuranoside.

13. A compound as in claim 1 which is ethyl-6-desoxy-6-(theophyll-7-yl)-2,3,4-tri-O-nicotinoyl-α-D-glucopyranoside.

14. A compound as in claim 1 which is methyl-6-desoxy-6-(theophyll-7-yl)-2,3,4-tri-O-benzoyl-α-D-glucopyranoside.

15. A pharmaceutical composition suitable for the treatment of hyperlipemia comprising a hypolipemically-effective amount of a compound as in claim 1 in combination with a pharmaceutically acceptable carrier.

16. A method of treating hyperlipemia in a patient suffering therefrom which comprises orally administering to said patient a hypolipemically-effective amount of a compound as in claim 1.

* * * * *